(12) United States Patent
Walsh et al.

(10) Patent No.: US 9,682,199 B2
(45) Date of Patent: Jun. 20, 2017

(54) PRIMING METHOD FOR INFUSION DEVICE

(71) Applicant: ANIMAS CORPORATION, West Chester, PA (US)

(72) Inventors: Ryan Walsh, Douglassville, PA (US); Daniel L. Baker, Drexel Hill, PA (US); Matthew Clemente, Downingtown, PA (US); William King, Aston, PA (US); Gerald Kuehl, Collegeville, PA (US)

(73) Assignee: ANIMAS CORPORATION, West Chester, PA (US)

( * ) Notice: Subject to any disclaimer, the term of this patent is extended or adjusted under 35 U.S.C. 154(b) by 706 days.

(21) Appl. No.: 14/098,967

(22) Filed: Dec. 6, 2013

(65) Prior Publication Data

US 2014/0171867 A1 Jun. 19, 2014

Related U.S. Application Data

(60) Provisional application No. 61/739,325, filed on Dec. 19, 2012.

(51) Int. Cl.
*A61M 5/50* (2006.01)
*A61M 5/142* (2006.01)
(Continued)

(52) U.S. Cl.
CPC ...... *A61M 5/5086* (2013.01); *A61M 5/14244* (2013.01); *A61M 2005/1402* (2013.01);
(Continued)

(58) Field of Classification Search
CPC ............ A61M 5/5086; A61M 5/14244; A61M 2005/1402; A61M 2039/1022; A61M 2205/6027; A61M 2205/14
See application file for complete search history.

(56) References Cited

U.S. PATENT DOCUMENTS 6,656,148 B2  12/2003  Das et al.
7,435,922 B1  10/2008  Wittig et al.
(Continued)

FOREIGN PATENT DOCUMENTS

WO  2005/049117 A2  6/2005
WO  WO2005/049117  *  6/2005
(Continued)

OTHER PUBLICATIONS

International Preliminary Report on Patentability issued in related International Patent Application No. PCT/US2013/076025, issued Jun. 23, 2015, 9 pages.
(Continued)

*Primary Examiner* — Theodore Stigell

(57) ABSTRACT

Described is drug infusion device and lineset for delivering medication. The novel pump and lineset described herein eliminate the ability of the pump and lineset from being primed when the cartridge reservoir is in fluid communication with the drug-delivering cannula, through which medication is delivered, is inserted into the skin of a patient. The system and method of the invention include a lineset having a plurality of electrical leads for allowing electrical communication between the infusion pump and the infusion set and for allowing the pump to determine whether the lineset is connected to the infusion set when a priming operation is initiated.

2 Claims, 3 Drawing Sheets

(51) Int. Cl.
*A61M 5/14* (2006.01)
*A61M 39/10* (2006.01)

(52) U.S. Cl.
CPC . *A61M 2039/1022* (2013.01); *A61M 2205/14* (2013.01); *A61M 2205/6027* (2013.01)

(56) References Cited

U.S. PATENT DOCUMENTS

| | | |
|---|---|---|
| 8,310,415 B2 | 11/2012 | McLaughlin et al. |
| 2008/0171967 A1* | 7/2008 | Blomquist ............ G06F 19/324 604/67 |
| 2012/0238849 A1 | 9/2012 | Holtzclaw et al. |
| 2016/0015957 A1* | 1/2016 | Tieck ................... A61M 5/142 604/533 |

FOREIGN PATENT DOCUMENTS

| | | | |
|---|---|---|---|
| WO | 2008/114220 A2 | | 9/2008 |
| WO | WO2008/114220 | * | 9/2008 |

OTHER PUBLICATIONS

International Search Report issued in corresponding International Patent Application No. PCT/US2013/076025, mailed Mar. 24, 2014.

* cited by examiner

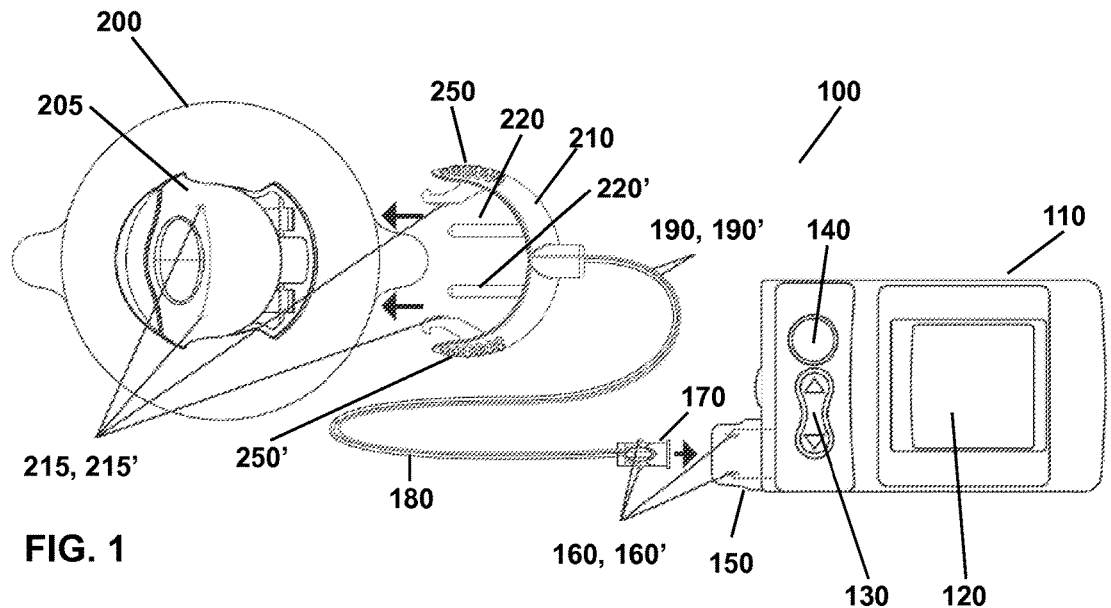
FIG. 1
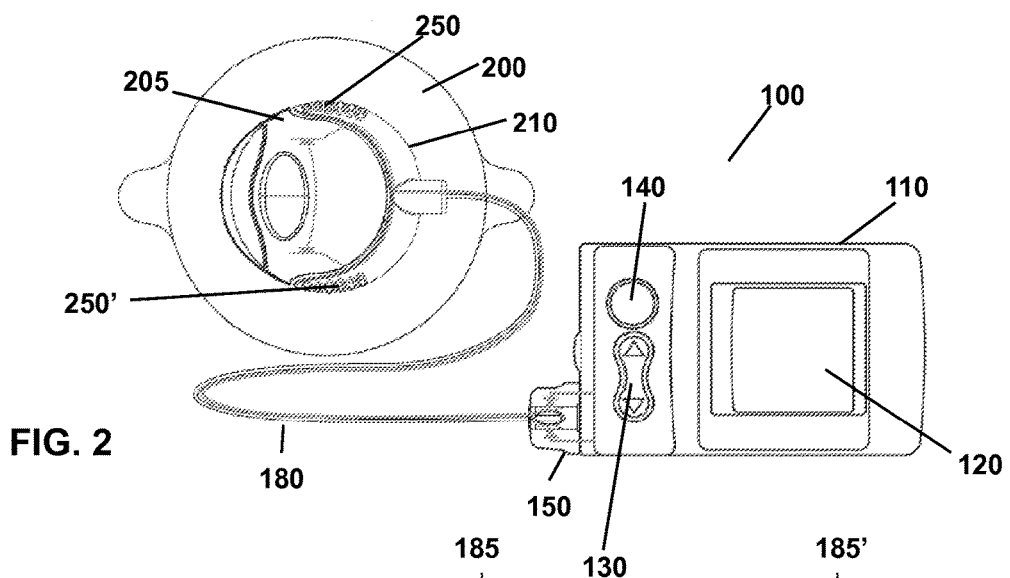
FIG. 2
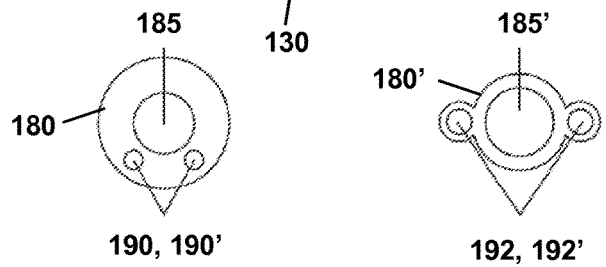
FIG. 3A
FIG. 3B

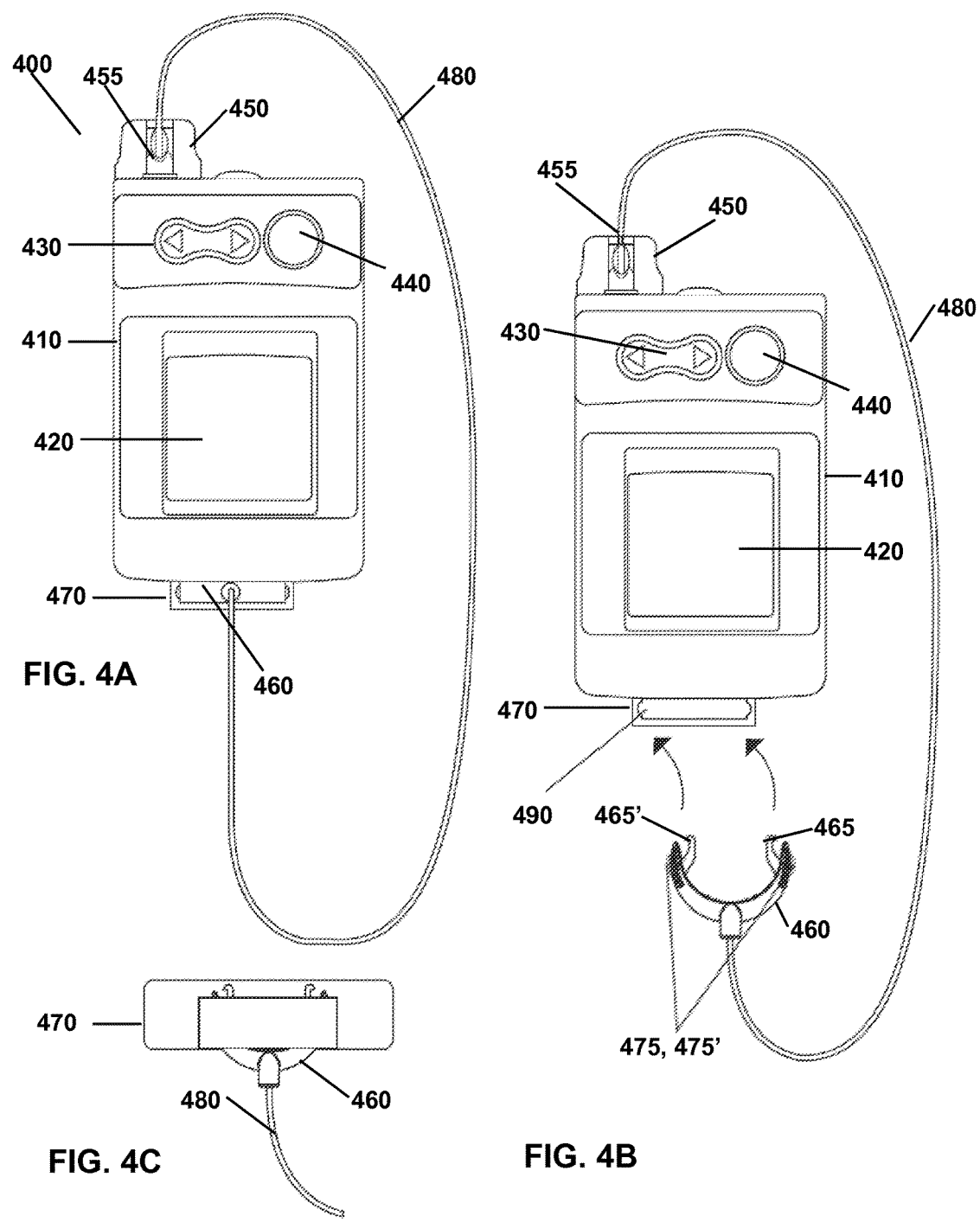

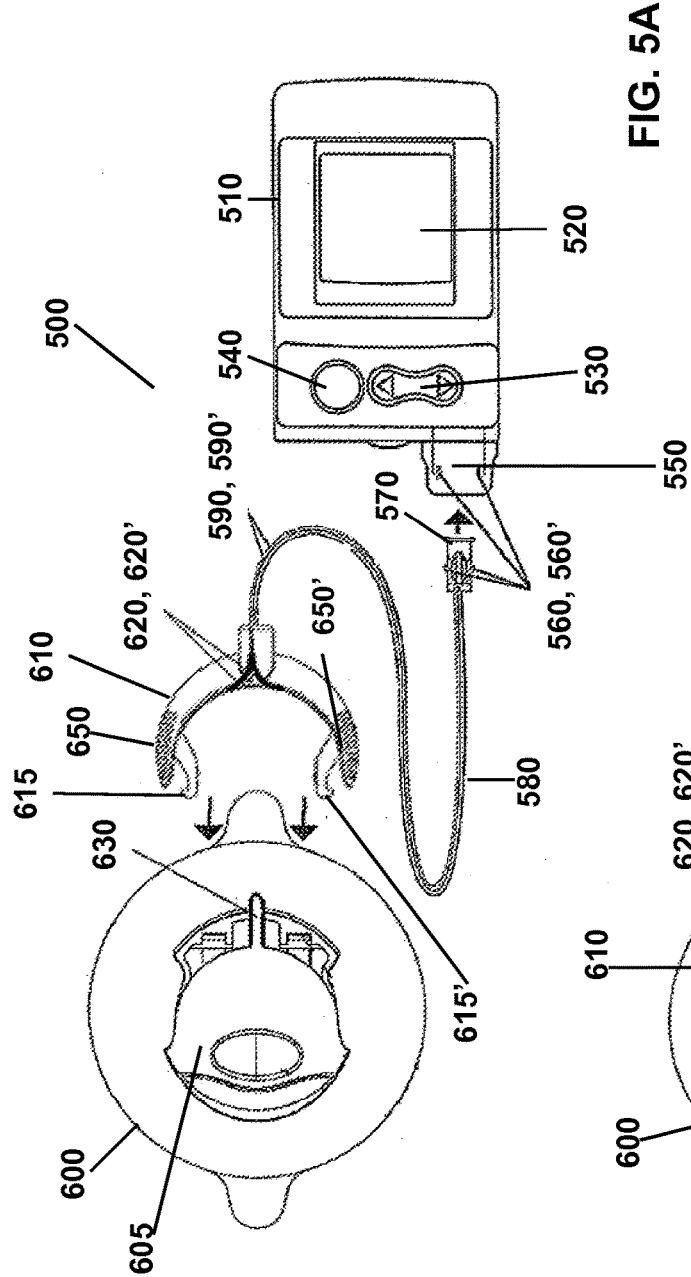
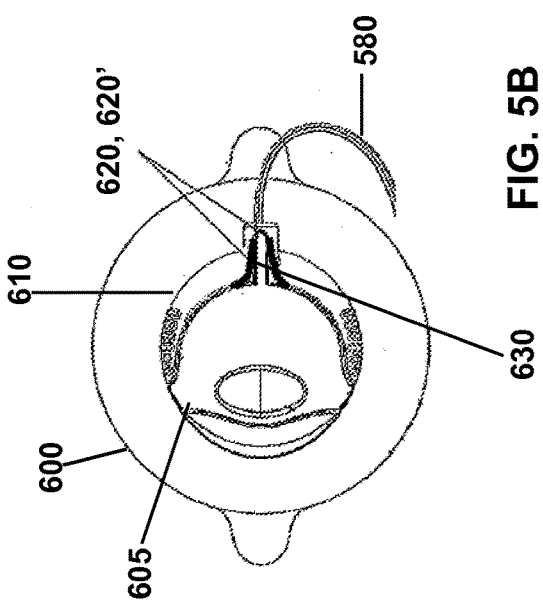
FIG. 5A
FIG. 5B

PRIMING METHOD FOR INFUSION DEVICE

CROSS REFERENCE TO RELATED APPLICATIONS

This application relates to U.S. patent application Ser. No. 61/739,325, filed Dec. 19, 2012; all applications are herein incorporated by reference in their entireties.

FIELD OF THE INVENTION

The present invention relates, in general, to drug delivery devices and, more particularly, to systems and methods for detecting whether the infusion device is connected to a patient when priming the reservoir and lineset of the device.

BACKGROUND OF THE INVENTION

The use of drug delivery devices for various types of drug therapy is becoming more common as the automated infusion of a drug may provide more reliable and more precise treatment to a patient.

Diabetes is a major health concern, as it can significantly impede on the freedom of action and lifestyle of persons afflicted with this disease. Typically, treatment of the more severe form of the condition, Type I (insulin-dependent) diabetes, requires one or more insulin injections per day, referred to as multiple daily injections. Insulin is required to control glucose or sugar in the blood, thereby preventing hyperglycemia that, if left uncorrected, can lead to ketosis. Additionally, improper administration of insulin therapy can result in hypoglycemic episodes, which can cause coma and death. Hyperglycemia in diabetics has been correlated with several long-term effects of diabetes, such as heart disease, atherosclerosis, blindness, stroke, hypertension, and kidney failure.

The value of frequent monitoring of blood glucose as a means to avoid or at least minimize the complications of Type I diabetes is well established. Patients with Type II (non-insulin-dependent) diabetes can also benefit from blood glucose monitoring in the control of their condition by way of diet and exercise. Thus, careful monitoring of blood glucose levels and the ability to accurately and conveniently infuse insulin into the body in a timely manner is a critical component in diabetes care and treatment.

To more effectively control diabetes in a manner that reduces the limitations imposed by this disease on the lifestyle of the affected person, various devices for facilitating blood glucose (BG) monitoring have been introduced. Typically, such devices, or meters, permit the patient to quickly, and with a minimal amount of physical discomfort, obtain a sample of their blood or interstitial fluid that is then analyzed by the meter. In most cases, the meter has a display screen that shows the BG reading for the patient. The patient may then dose themselves with the appropriate amount, or bolus, of insulin. For many diabetics, this results in having to receive multiple daily injections of insulin. In many cases, these injections are self-administered.

Due to the debilitating effects that abnormal BG levels can have on patients, i.e., hyperglycemia, persons experiencing certain symptoms of diabetes may not be in a situation where they can safely and accurately self-administer a bolus of insulin. Moreover, persons with active lifestyles find it extremely inconvenient and imposing to have to use multiple daily injections of insulin to control their blood sugar levels, as this may interfere or prohibit their ability to engage in certain activities. For others with diabetes, multiple daily injections may simply not be the most effective means for controlling their BG levels. Thus, to further improve both accuracy and convenience for the patient, insulin infusion pumps have been developed.

Insulin pumps are generally devices that are worn on the patient's body, either above or below their clothing. Because the pumps are worn on the patient's body, a small and unobtrusive device is desirable. Some devices are waterproof, to allow the patient to be less inhibited in their daily activities by having to remove their drug infusion device while showering, bathing, or engaging in various activities that might subject their infusion device to moisture, such as swimming, and when priming the fluid delivery system—such as when a cartridge is replaced or a reservoir is refilled—to remove air from the fluid path.

In such devices, it would be desirable to have a structure and method for verifying that the cannula through which the medicament is delivery to the subcutaneous or intradermal space is removed from the patient prior to beginning the priming process to avoid excess or unintended dosing of medication into the patient.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 1 illustrates an exemplary embodiment of a drug infusion device according to the present invention, in top plan view.

FIG. 2 illustrates another exemplary embodiment of a drug infusion device according to the present invention, in top plan view.

FIGS. 3A-3B illustrate cross-sectional views of an embodiment of the lineset of the present invention.

FIGS. 4A-4C illustrate views of another embodiment of an exemplary device according to the present invention in various states of the priming sequence of the present invention.

FIGS. 5A-5B depict an illustrative embodiment of the attachment and removal of a lineset from an infusion set according to the present invention.

DETAILED DESCRIPTION OF THE INVENTION

In an exemplary embodiment, the invention is directed to structures and methods for avoiding the accidental or unintentional dosing of medication from a portable drug infusion device during a priming operation.

Most portable drug infusion pump reservoirs are similar in design or concept to that of a standard syringe. The reservoir is typically comprised of two major components; a cylindrical barrel, with a connector integrated into the distal end for attachment of an infusion line set, and a movable plunger with an elastomer seal. The plunger is inserted into the open proximal end of the barrel to form a closed volume. To deliver drug, a mechanically driven piston is advanced forward, which in turn advances the cartridge plunger forward, reducing the internal volume of the cartridge, thus displacing fluid. Typically, the piston (part of the durable device) is not mechanically interlocked with the cartridge plunger because there is no need to retract the plunger after the cartridge has been filled and subsequently installed in the pump or upon exhaustion of the contents of the cartridge.

In the typical application, the cartridge is filled to a predetermined volume that is somewhat smaller than the total internal volume of the reservoir, leaving a small amount of space containing air. Further, the lineset attached to the cartridge that allows for fluid communication between the cartridge and a cannula that is inserted through the patients skin into the subcutaneous space also contains air that must be purged from the system, prior to being able to deliver the medicament from the cartridge into the cartridge.

Failing to purge the system of air, during a process known to those in the art as priming, may result in inaccurate medication delivery, since while the infusion device may be operating, a portion of the volume being delivered to the patient may simply be air. Therefore, the pump system must be primed prior to use. During the priming process, the motor of the insulin infusion device runs to advance the plunger into the cartridge and expel insulin through the lineset and cannula to remove air from the system. However, in some instances, the patient may neglect removing the cannula from insertion into their body prior to priming, risking serious consequences due to drug overdose by unintentionally infusing medication into their body during the priming process. With certain medication, such as insulin, the excess dosing of just a small amount of medication can cause serious side-effects, such as hypoglycemia, which can be extremely injurious or even fatal.

The present invention, therefore, is directed to a system and method for ensuring that the patient is disconnected (i.e., the cannula is removed from their body) prior to priming their infusion device.

FIG. 1 illustrates a method which would enable a pump to detect whether the line set is connected or disconnected from an infusion set. Referring to the illustrated infusion system 100, an infusion device 110 may include a screen display 120 and a keypad 130 with an "Enter" or "Execute" button 140 for displaying information and entering data, scrolling through menu screens, etc. A typically infusion pump according to this invention will have a microprocessor, memory, and software user interface. Illustrative infusion devices include those described in U.S. Pat. No. 6,656,148; U.S. Pat. No. 7,435,922; and U.S. Pat. No. 8,310,415, all of which are hereby incorporated by reference in their entireties.

The cartridge cap 150 secures a cartridge containing medication in a cartridge cavity within the infusion device (also referred to herein and synonymously as a "pump"). The cartridge cap according to this embodiment of the invention includes multiple housing contacts 160' that are in electrical communication with the pump's microprocessor. A luer connector 170 attaches to the proximal end of the lineset 180 that carries medication from the cartridge to the infusion set 200 that attaches to a patients skin, usually via an adhesive patch is configured to releasably attach to the cartridge. Exemplary methods for attaching luer connectors to cartridges include threaded and bayonet style connections.

In this embodiment, the conductive, housing contacts 160', found in the housing of the pump 110 or (as shown) in the cartridge cap 150 connect with conductive lineset contacts 160 on the luer connector 170 of the line set. These conductive surfaces can be embedded through co-molding a conductive material, such as resins containing graphite, other co-molded plastics which could be plated, such as a platable ABS, or through other methods such as metallic inlays. These surfaces then connect to electrical wires 190, 190' that are co-extruded into the tubing of the lineset 180, creating an electrical connection to the distal end of the lineset 180 where they connect to conductive prongs 220, 220' found in the connector 210 of the infusion set 200. When the connector 210 is not connected to the infusion set 200, as seen in FIG. 1, the circuit is open. When the connector 210 is connected to the infusion set 200 the conductive prongs 220, 220' of the connector 210 are inserted into contact plugs (not shown) in the upper housing 205 of the infusion set 200. A secure, releasable attachment is made between the connector 210 and the upper housing 205 of the infusion set 200, as shown illustratively in this embodiment of the invention, by a pair of securing tabs 215' prime protruding from the connector 210. When the connector 210 is inserted into the upper housing 205, the securing tabs 215' bias inward and latch with mating tabs 215 (not shown) that are located inside the upper housing.

In order to release the device, the patient or healthcare provider might place a thumb and forefinger on textured grips 250, 250' and squeeze the textured grips 250, 250' together to release the securing tabs 215' from the mating tabs 215, allowing the connector 210 to be pulled out of the upper housing 205 of the infusion set 200.

In one embodiment, the contact plugs in the upper housing 205 of the infusion set 200 are in electrical communication with one another. Thus, when the connector 210 is inserted into the upper housing 205, the conductive prongs 220, 220' are short-circuited by being inserted into the contacts plugs, creating a closed circuit. A sensor (not shown) such as a simple conductivity sensor in the pump housing 110 may be connected to the housing contacts 160'. The sensor can detect whether the connector 210 is connected to the infusion set 200 based on whether it senses an open circuit (lineset disconnected) or closed circuit (lineset connected) and send a signal to the microprocessor that controls the infusion system. The microprocessor may be programmed to disable the priming sequence when the sensor senses a closed circuit, thereby inhibiting the possibility of the device being primed while connected to the patient.

FIG. 2 illustrates the device with the connector 210 attached to the upper housing 205 of the infusion set 200. According to this embodiment of the invention, the circuit detected across the housing contacts 160' (as shown in FIG. 1) would be closed. The sensing of this closed circuit could, therefore, be used to disable the priming sequence or allow the pump to confirm and display that the patient's infusion set is connected.

The flexible lineset tubing 180 is illustrated in cross-section in FIGS. 3A and 3B. FIG. 3A shows the lineset 180 with a central fluid path 185 having two electrical wires 190, 190' formed within the wall of the lineset 180. FIG. 3B shows an alternative configuration wherein the electrical wires 192, 192' are encased within insulation or other sheathing and attached to the sides of the lineset 180' with a central fluid path 185'.

To use the disclosed embodiments of the invention in an illustrative manner, the user may attempt to begin the priming sequence on the pump. The pump might first produce a low current signal through the electrical pathway described which, in turn, may detect whether the circuit is open or closed. If the circuit is closed the pump does not begin the priming sequence and warns the user to disconnect the line set before priming. Once the connector is removed from the infusion site and priming sequence is completed, the user will then be able to re-attach the line set and pump delivery can be initiated.

FIGS. 4A-4C illustrates an embodiment of the present invention where a harness 470 is attached to the housing of the infusion pump 410. As shown in FIG. 4A, the infusion pump 410 may include a data entry keypad 430 and a confirmation button 440 to allow the user to interface with the device's menus and other messages that might appear on the display 420.

In this embodiment, the infusion system 400 includes an infusion set connector 460 that must be physically attached to a docking station (i.e., the harness 470) on the pump 410, in order to initiate the priming sequence. The determination whether to initiate priming is, therefore, based on whether the connector 460 is physically attached to a harness 470 attached to the infusion pump 410. Thus, line set 480 does not require electrical wires, obviating the need for contacts in the cartridge cap 450 or luer connector 455, and reducing the number of parts, complexity, and costs associated with this embodiment, but without providing certainty regarding whether the connector 460 is connected to an infusion set, as is possible with the previously described embodiments.

As shown in FIG. 4B, the connector 460 having attachment tabs 465, 465' contains small magnets 475, 475' embedded into the arms of the connector 460. The small magnets 475, 754' provide the harness 470 a method for confirming that the connector 460 is attached to the harness 470. The sensor technology to detect these magnets on the connector could be a Hall Effect sensor 490 or multiple sensors that can detect the proximity of the small magnets 475, 475'. Similarly, other known methods of detecting the engagement of the connector could be used, such as a simple contact switch or optical sensor. In any case, confirmation that the connector 460 is attached to the harness 470, as shown in FIG. 4C, is transmitted to the microprocessor in the infusion pump 410 that may then enable the priming sequence or, if it cannot be determined that the lineset is disconnected from the patient, a warning, error, or alert message reminding the patient or user of the steps to be taken to initiate a priming sequence.

FIGS. 5A and 5B illustrate yet another embodiment of the invention. In this embodiment, a sensor may be placed in the housing of the infusion pump 510 of the infusion system 500. The infusion pump 510 includes a screen display 520, data entry keypad 530, a confirmation button 540, and a microprocessor. The microprocessor has a quantity of one or both of random access memory (RAM) and read-only memory (ROM) and may have a priming sequence pre-programmed in RAM or ROM. The microprocessor is in electrical communication with the housing contacts 560' located in or proximate to the cartridge cap 550, or the microprocessor is in electrical communication with a sensor in the housing that is in electrical communication with the housing contacts. The housing contacts 560' create an electrical contact with lineset contacts 560 when the luer connector 570 is attached to the cartridge in the infusion pump 510, as shown in FIG. 5A.

The lineset 580 would include electrical wires 590, 590' that terminate with separate connector contacts 620, 620' in the infusion set connector 610. The connector contacts 620, 620' are configured to be in contact when the connector 610 is not attached to the upper housing 605 of the infusion set 600. The infusion set connector 610 is inserted into the upper housing 605 of the infusion set 600 and releasably connected thereto by attachment tabs 615, 615' and texture grips 650, 650'. When the upper housing 605 and connector 610 are engaged, as shown in FIG. 5B, a separator 630 biases the connector contacts 620, 620' apart, breaking the electrical contact between them.

A sensor in the housing of the infusion pump 510 that is in contact with the housing contacts 560, 560' should detect an open signal when the connector 610 is attached to the upper housing 605 of the infusion set 600. When the open signal is detected, it may send a signal to the pump's microprocessor that will, in turn, disable the priming sequence, or take other such action that requires a determination as to whether the infusion set 600 is connected to the pump 510 via the connector 610 and lineset 580.

The same electrical pathway could be used to transmit a signal from a sensor, such as a continuous glucose monitoring sensor, which is co-located on the infusion site. Similar circuit methods could also detect if the device is fully actuated, where the activation of the infusion set would open or close the electric circuit. Signals could also be sent from the pump to the infusion set triggering the activation of the device through known methods.

It will be recognized that equivalent structures may be substituted for the structures illustrated and described herein and that the described embodiment of the invention is not the only structure, which may be employed to implement the claimed invention. In addition, it should be understood that every structure described above has a function and such structure can be referred to as a means for performing that function. While embodiments of the present invention have been shown and described herein, it will be obvious to those skilled in the art that such embodiments are provided by way of example only. Numerous variations, changes, and substitutions will now occur to those skilled in the art without departing from the invention.

It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A medical infusion system, comprising:
an infusion pump having a housing, a cartridge for holding medication, a cartridge cap for securing the cartridge to the housing, at least two housing contacts disposed proximate to the cartridge cap, a microprocessor having a pre-programmed priming sequence, and a conductivity sensor within the housing in electrical communication with the microprocessor and the at least two housing contacts;
an infusion set comprising an adhesive patch and an upper housing attached to the adhesive patch, and at least two contact plugs, the at least two contact plugs in electrical communication with one another;
an infusion set connector releasably attachable to the upper housing;
at least two connector contacts in the connector configured for electrical communication with the at least two contact plugs when the connector is attached to the upper housing;
a lineset comprising flexible tubing attached to the connector;
at least two electrical wires contained within or attached to the lineset, each of the at least two electrical wires in electrical communication with one of the at least two connector contacts;
a luer connector attached to the lineset releasably attachable to the cartridge cap;
at least two lineset contacts disposed proximate to the luer connector, wherein a closed electrical circuit is detected across the at least two lineset contacts when the infusion set connector is attached to the upper housing or an open electrical circuit is detected across the at least two lineset contacts when the infusion set connector is not attached to the upper housing; and wherein the pre-programmed priming sequence is disabled when the conductivity sensor detects a closed circuit across the housing contacts.

2. The medical infusion system of claim 1, wherein the pre-programmed priming sequence is enabled when the conductivity sensor detects an open circuit across the housing contacts.

\* \* \* \* \*